United States Patent [19]

Tagaya

[11] Patent Number: 4,551,022
[45] Date of Patent: Nov. 5, 1985

[54] TESTING METHOD BY A SPECTROSCOPIC PHOTOMETRY USING THREE WAVELENGTHS OF LIGHT AND A DEVICE FOR SAID METHOD

[75] Inventor: Ryosaku Tagaya, Gunma, Japan

[73] Assignee: Eisai Co., Ltd., Tokyo, Japan

[21] Appl. No.: 463,106

[22] Filed: Feb. 2, 1983

[30] Foreign Application Priority Data

Jun. 3, 1982 [JP] Japan .................. 57-094011

[51] Int. Cl.$^4$ ............................ G01J 3/50
[52] U.S. Cl. ..................... 356/406; 250/226; 250/223 B; 356/414; 356/416; 356/240; 356/407
[58] Field of Search ............... 356/300, 405, 406, 407, 356/414, 416, 426–428, 240; 250/223 B, 226

[56] References Cited

U.S. PATENT DOCUMENTS

| | | |
|---|---|---|
| 2,479,743 | 8/1949 | Hall et al. ............... 356/416 X |
| 3,777,169 | 12/1973 | Walter et al. |
| 3,961,898 | 6/1976 | Neeley et al. ............... 346/33 A X |
| 4,029,416 | 6/1977 | Hawes ............... 356/51 |
| 4,257,709 | 3/1981 | Mostyn, Jr. ............... 356/435 |
| 4,300,689 | 11/1981 | Franklin et al. ............... 250/223 B |

Primary Examiner—F. L. Evans
Attorney, Agent, or Firm—Flynn, Thiel, Boutell & Tanis

[57] ABSTRACT

For detecting a leaking in a transparent or semi-transparent vessel by the dye bath method, the light passing through the vessel is divided into three wavelength regions, that is light having the characteristic wavelength of the dye bath liquid, the light having a wavelength shorter than said light as much as prescribed wavelength and the light having a wavelength longer than said light as much as prescribed wavelength, the curvature of transmittance curve based upon difference value of transmittance among three light having different wavelength is obtained for comparing with a preestablished value to judge the vessel to be inferior or normal with the compared output.

6 Claims, 4 Drawing Figures

TESTING METHOD BY A SPECTROSCOPIC PHOTOMETRY USING THREE WAVELENGTHS OF LIGHT AND A DEVICE FOR SAID METHOD

BACKGROUND OF THE INVENTION

The present invention relates to a testing method and a device for the testing method according to a spectrophotometry using three wavelengths of light in which a leaking in a vessel is detected, specifically a leaking in an ampoule is detected with a dye bath technique for example blue bath method.

When a pinhole is brought about in a glass ampoule or a vial for a liquid of chemical or food, or when an ampoule is not perfectly sealed hermetically, the leakage or the bacillary pollution may be caused.

Accordingly, the dye bath technique such as blue bath method is utilized, in which when an ampoule is dipped into a dense blue dye solution, for example a solution of methylene blue or other blue dye for food, evacuated once and then brought back to the normal pressure, if the ampoule is inferior the dense dye solution is introduced into the ampoule through small holes, cracks or gaps of the glass wall. An inferior ampoule is eliminated by detecting the colour of the introduced dye solution. Conventionally such ampoule containing dye solution has been found by the visual inspection of the colour of dye solution in the ampoule. There has been a detection limit for this method. Further, it has been difficult to detect in case of coloured ampoule or coloured solution.

Therefore, for measuring the light energy transmitted through the ampoule as an optical detection method, the measuring method by two-wavelength spectrophotometry is set for in Japanese Patent Application S54-133183 (Priority U.S. Ser. No. 869554).

In the measuring method by two wavelength spectrophotometry, the light passing through a vessel and a content in the vessel is received, and divided into two fluxes with optical cables. A standard filter is provided for one flux to filter a light of wavelength uninfluenced by the characteristic wavelength as of the dye and a target filter being provided for the other flux to filter the characteristic wavelength of the dye.

The outputs from filters are detected as electric signals. These two output signals are mutually added and subtracted for obtaining the sum and the differential. In comparison with these values, the subject is judged to be good or inferior.

However, even in the measurement by the two wavelength spectrophotometry, when the vessel such as an ampoule is coloured for example in brown, the difference in colour of the individual ampoule make the absorption in the wavelength for the measurement change, therefore, even for a good ampoule is judged to be out of the judging region for a good one resulting to an inferior detection sensitivity.

Further, in case of the ampoule containing coloured liquid, the temperature change of the content itself causes the absorption to change, affecting the result of measurement.

BRIEF SUMMARY OF THE INVENTION

The object of the present invention is to decrease the influence of change in the absorption caused by the dispersion of degree of colouring of a coloured ampoule (for example, a so called Amber ampoule) and the temperature change.

As the amber ampoule is employed for eliminating shorter wavelength, the delicate difference in the degree of colouring causes the absorption in a shorter wavelength region to be measured incorrectly. The influence of the wavelength characteristic cannot be avoided in the conventional two wavelength spectrophotometry as described above.

Another object is to decrease influence of the change of absorption corresponding to the temperature of the content when the characteristic wavelength of the ampoule itself is in the measuring wavelength region.

For example, as shown in FIG. 1 curves are obtained from measurement of transmittance for a vacant ampoule coloured in dense brown F(R) and a vacant ampoule coloured in comparatively light brown F(O). The transmittance values of the lightly coloured vacant ampoule F(O) at wavelength values of 570 nm, 630 nm and 720 nm are respectively expressed by a1, a2 and a3, and those of the densely coloured vacant ampoule F(R) at the same wavelength as for F(O) by b1, b2 and b3.

The differential of F(R) and F(O) in the vicinity of the wavelength of 550~600 nm and those in the vicinity of 600~650 nm and 700~750 nm are different from each other, and the gradient of a line connecting a1 and a3, at a1 is different from that of a line connecting b1 and b3 at b1. However, these curves are similar in form. The wavelength of 630 nm is the characteristic wave length of the dye (Food blue No. 1). The wavelength of 570 nm and that of 720 nm are the standards set for comparison.

In case of measurement using two wavelengths, if the transmittance at the wavelength of 630 nm and that at the wavelength of 720 nm are compared, the differential (a3-a2) for the lightly coloured ampoule F(O) is smaller than the differential (b3-b2) for the densely coloured ampoule F(R). Although vacant ampoules which are not affected entirely by contents are used, such difference as described is caused, which may be beyond the quality judging region making the accuracy of judgement inferior.

However, when the measurement using three wavelengths according to the present invention is employed, the measurement results is not practically affected by the colouring degree of the ampoule. Accordingly, the form of transmittance curve is not influenced by the colouring degree of the ampoule. Particularly, when y is the intersection of the vertical line at the wavelength of 630 nm and the straight line connecting a3 and a1, a differential (a2-y) is expressed as (A), which is so called a depth of curve of the empty ampoule F(O). The depth of curve is a value for nearly determining the curvature of the curve. For the empty ampoule F(R), x is the intersection of the vertical line at the wavelength of 630 nm and the straight line connecting b3 and b1, being expressed as (B). The form and the depth of curve of the empty ampoule F(O) is almost the same as those of the empty ampoule F(R), therefore (A) is nearly equal to (B).

Thus, the depth of curve (A) and that of (B) are not so influenced by the degree of colouring of the ampoule. Therefore, when Food blue No. 1 is employed for example as a dye for blue bath, an inferior ampoule which the dye leaked into has its absorption increased and its transmittance decreased, and the depth of curve takes a smaller value compared with said differential (A) or (B) as a fixed standard value. If the ampoule having a characteristic as this is judged as an inferior one, a exact selection is performed without being affected by the gradient of curve and the absolute value of transmittance.

In FIG. 2, there are shown the transmittance characteristic (P) of the coloured content liquid at the room temperature (18° C.) and the transmittance characteristic (Q) of the same liquid heated to 60° C. As obvious from the FIG. 2, at a high temperature the change in the transmittance characteristic (Q) in the longer wavelength and the shorter wavelength is symmetric with the characteristic wavelength 630~670 nm as a symmetric axis. However, the form of (P) and (Q) is almost the same.

The measured transmittance at 18° C. of the coloured liquid at the wavelength of 570 nm, 630 nm and 720 nm is respectively expressed as C1, C2 and C3, and the same at 60° C. as d1, d2 and d3. When the intersection of the straight line connecting C1 and C3, and the vertical line at the wavelength of 630 nm is k, the differential of C2 and k is taken as (C). Similarly, when the intersection of the straight line connecting d1 and d3, and the vertical line at the wavelength of 630 nm is 1, the differential of d2 and 1 is taken as (D). The differential (C) is almost equal to the differential (D). Accordingly, if (C) and (D) are taken as the standard value, the value of the transmittance of an inferior ampoule in which the dye bath liquid leaked is lower than said standard value for easy judgement.

Selection of three points in wavelength may be performed at will according to the characteristic wavelength of a dye of dye bath, and an ampoule or a content in the ampoule regarding that the peak value of methylene blue is in the vicinity of 660 nm and the peak value of Blue No. 1 dye for food is in the vicinity of 630 nm.

Other and further objects and features of the present invention will be apparent from the following description taken in connection with the accompanying drawings.

DETAILED DESCRIPTION

An embodiment of the testing device according to the present device will be described referring to FIGS. 3 and 4.

Figure 3:
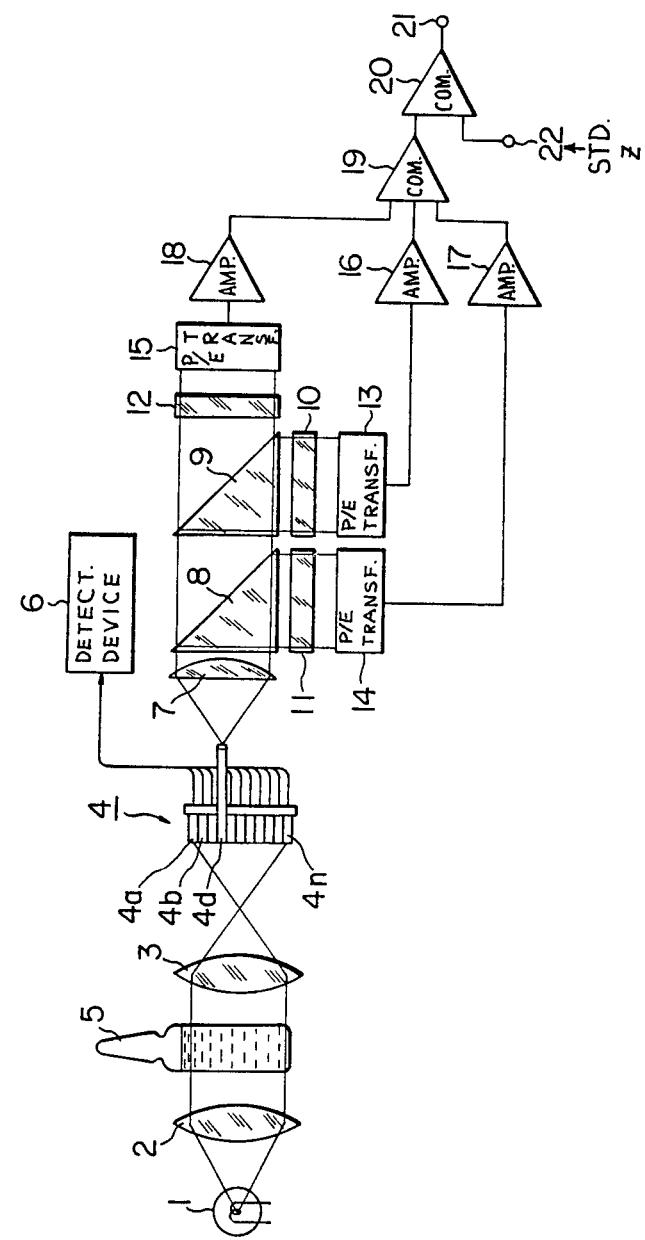
FIG. 3 is a schematic diagram showing an embodiment of the testing device according to the present invention.

In FIG. 3, (1) is projector lamp as a light source. For the projector lamp, an objective lens (2), a focussing lens (3) and a light receiving member (4) are sequentially arranged. An ampoule as a subject to be tested is put between said objective lens (2) and focussing lens (3).

Said light receiving member comprises micro light receivers (4a), (4b), . . . such as light guides divided into a plural number of small sections like glassfibers corresponding to detection limit of foreign matters. The output side of respective micro-light receivers (4a), (4b), . . . is connected to a detection device (6) of foreign matters in the ampoule (5). A light guide (4d) for example for one bit is introduced from one section of micro-light detectors (4a), (4b), . . . . On the tip of the light guide (4d) two prism filters, the 1st and the second filters, are provided through a condenser (7). The light beam passed through the condenser (7) is divided into three, one refracted by the 1st prism filter (8), one refracted by the 2nd prism filter (9) after passing through the 1st prism filter and one passed the 1st and 2nd prism filters. A wavelength filter (10) for selecting the characteristic wavelength of the dye bath liquid is provided for the refracted light by the 2nd prism filter. For the refracted light by the 1st prism filter (8) and the light passed through the 1st and 2nd filters, respective standard wavelength filters (11) and (12) are provided. The output side of respective wavelength filter (10), (11) and (12) is connected to a comparator (19) through photoelectric transfer elements (13), (14) and (15), and amplifiers (16), (17) and (18). The comparator (19) is connected to an output terminal (21) through a comparator (20). The other input side of the comparator (20) is connected to an input terminal (22) for inputting a standard value for judgement (Z) which is prescribed to correspond to said differential ($A \approx B$).

Figure 4:
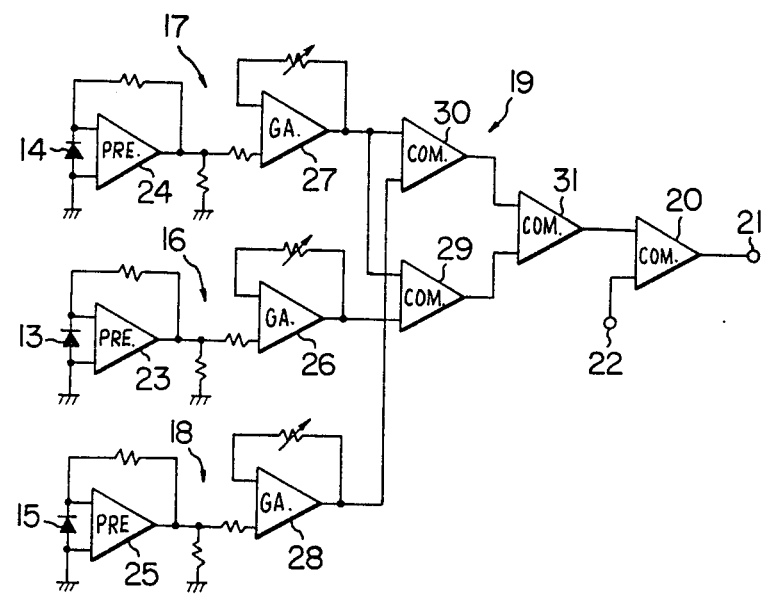
FIG. 4 is a block diagram to illustrate a concrete embodiment of the electric circuit member of the testing device according to the present invention.

A concrete circuit following photoelectric transfer elements (13), (14) and (15) in FIG. 3 is shown in FIG. 4, in which (13), (14) and (15) are shown in FIG. 4, in which (13), (14) and (15) are photoelectric transfer elements of photodiodes. These elements output electric signals corresponding to the transmittance of the light of which wavelength is for example 630 nm, 570 nm and 720 nm. These photoelectric transfer elements (13), (14) and (15) are connected to preamplifiers (23), (24) and (25), and gain adjusting amplifiers (26), (27) and (28) composing said amplifiers (16), (17) and (18). Among these gain amplifiers (26), (27) and (28), two gain amplifiers (26) and (27) are connected to a comparator (29), gain amplifiers (27) and (28) being connected to a comparator (30), and further, these comparators (29) and (30) are connected to a comparator (31) and to said comparator (20) through said comparator (31). Said comparators (29), (30) and (31) compose the comparator (19) in FIG. 3.

The action of the device according to the present invention will be described hereinafter.

In FIG. 3 an ampoule (5) as a subject to be tested is dipped into a dense blue dye solution such as methylene blue or blue dye for food and then made vacuum. The dense dye solution will be introduced into the ampoule through some of pinholes, cracks and gaps if the ampoule have any of these faults. The ampoule thus pretreated is set continuously between the objective lens (2) and focussing lens (3) by a supply device (not shown). The ampoule (5) thus set is revolved in a high speed and stopped quickly. A foreign substance, if any mixed into the solution will float for being detected by any one of micro-light receivers (4a), (4b), . . . , a signal obtained by the detection is inputted to the foreign substance detecting device (6) to eliminate the ampoule, which contains the foreign substance.

When the ampoule itself has pinholes and the like and the dense dye solution is introduced into the ampoule, the light transmitted through the ampoule is coloured, the coloured light is introduced to the light guide (4d) to irradiate from the tip of it. The irradiated light made parallel by the condenser (7) passes through the 1st prism filter (8), being refracted by the 2nd prism filter (a), passing through the wavelength filter which selects the characteristic wavelength of the dye bath liquid, being transformed into a electric signal in the photoelectric transfer element (13), and is transmitted to the comparator group (19) through the amplifier (16). In the comparator group (19), said signals obtained in a similar way for the standard are measured for absorption values, or transmittance values of three wavelengths for comparison. The results value computed from these comparison is outputted as an analogue signal.

Particularly, respective output signals corresponding to transmittance of rays at the wavelength of 630 nm, 570 nm and 720 nm are amplified by respective preamplifier (23), (24) and (25) having their gain adjusted by gain adjusting amplifiers (26), (27) and (28) for being inputted to comparators (29) and (30).

Figure 1:
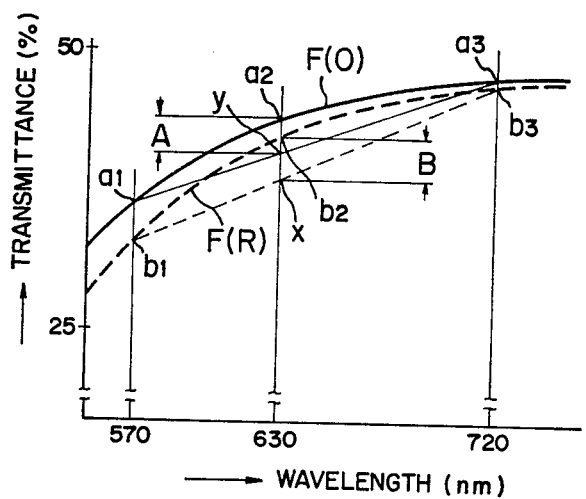
FIG. 1 shows transmittance characteristic curve of a densely coloured empty ampoule and a light coloured empty ampoule.
Figure 2:
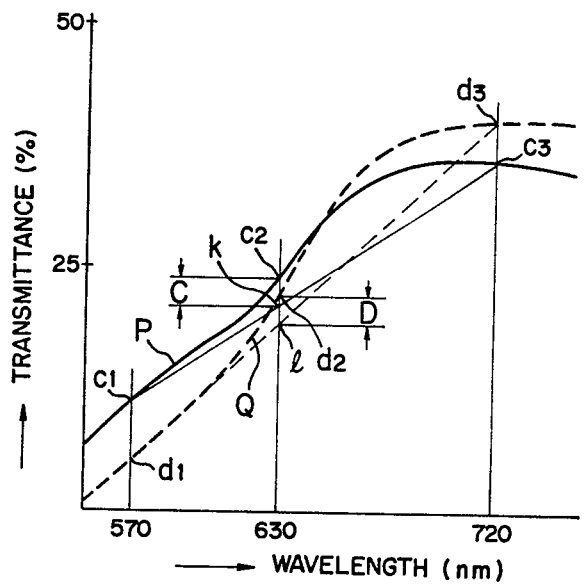
FIG. 2 shows transmittance characteristic curves of a coloured content in an ampoule at the room temperature (18° C.) and that in the heated state (60° C.).

Now, for obtaining the differential (A) of the ampoule F(O) in FIG. 1, y is obtained as the following:

$$y = \frac{630 - 570}{720 - 570} \times (a3 - a1) + a1 = \frac{6}{15}(a3 - a1) + a1$$

therefore, the differential (A) is $$A = a2 - y = a2 - \left\{ \frac{6}{15}(a3 - a1) + a1 \right\} = (a2 - a1) - \frac{6}{15}(a3 - a1)$$

Basing upon the formula, the comparator (30) is inputted with output (a1) at the wavelength of 570 nm and output (a3) at the wavelength of 720 nm for outputting 6/15(a3-a1), which is the differential (a3-a1) multiplied by a constant (6/15) and gainadjusted. The comparator (29) is inputted with the output (a1) at the wavelength of 570 nm, and the output (a2) at the wavelength of 630 nm, outputting the differential (a2-a1). And then, in the comparator (31) the differential of these outputs (a2-a1) and 6/15(a3-a1) is obtained for outputting an output.

$$A = (a2 - a1) - \frac{6}{15}(a3 - a1)$$

In a similar way, the differential (C) for the characteristic curve (P) can be obtained to be outputted from the comparator (31) as;

$$C = (C2 - C1) - \frac{6}{15}(C3 - C1)$$

The differential (A) or (C) thus obtained is compared with the judging standard value (Z) inputted from the input terminal (22). When said differential (A) or (C) is lower than the standard value (Z), a signal that judges an ampoule to be inferior is outputted from the comparator and a solenoid and the like (not shown) are excited for eliminating the inferior ampoule.

What is claimed is:

1. A testing method using a spectrophotometry of three wavelength values for optically detecting a leak in a transparent or semitransparent vessel by a dye bath method, comprising the steps of: passing a light through said vessel; dividing into three parts the light which has passed through the vessel, said parts being (1) a light having the characteristic wavelength of the dye bath liquid, (2) a light having a wavelength shorter than the characteristic wavelength of dye bath liquid by a prescribed wavelength, and (3) a light having a wavelength longer than the characteristic wavelength of the dye bath liquid by a prescribed wavelength; and measuring the value of the light transmitted through the vessel at each of these three wavelengths; obtaining a transmittance curve from the transmittance values at these three wavelengths; comparing the curvature of said transmittance curve with a prescribed value; and judging whether the vessel is good or inferior from the comparison.

2. A testing method using a spectrophotometry of three wavelength values as claimed in claim 1, wherein said step of obtaining a transmittance curve includes plotting said transmittance values versus wavelength; said step of comparing includes connecting with a straight line the transmittance values of the light having a shorter wavelength and the light having a longer wavelength, and intersecting said straight line with a line at the wavelength of the dye bath liquid, and determining the curvature of said transmittance curve from the difference between the transmittance value at said intersection and that of the dye bath liquid at the wavelength of the dye bath liquid so as to determine the curvature of the curve.

3. A testing apparatus using a spectrophotometry of three wavelength values for optically detecting a foreign substance in a coloured liquid in a transparent or semitransparent vessel and flaws in the vessel, comprising: a light source; a light receiving member for receiving a light flux from the light source passing through a vessel or a liquid in the vessel; three optical filter means for generating optical signals in three selected wavelength regions from the flux from the light receiving member; three optical detector means for providing three output signals respectively representing the optical signals from said three optical filter means; and comparator means for mutual comparison of said output signals to obtain a compared value and for comparison of said compared value with a prescribed standard value for judgement.

4. A testing apparatus using a spectrophotometry of three wavelength values as claimed in claim 3, wherein said three optical filter means comprises 1st and 2nd prism filters disposed in series along said light flux, and respective wave filters for selecting respective specific wavelength values from (1) a light refracted from the 1st prism filter, (2) a light refracted from the 2nd prism filter after passing through the 1st prism filter and (3) a light passing through both the 1st and the 2nd prism filters.

5. A testing apparatus using a spectrophotometry of three wavelength values as claimed in claim 3, wherein said comparator means comprises a first comparator for providing a differential of transmittance values for a light of the characteristic wavelength of the coloured liquid and for a light having a wavelength shorter by a prescribed wavelength than the characteristic wavelength of the coloured liquid, a second comparator for providing a differential of transmittance values for a light having a wavelength longer by a prescribed wavelength than the characteristic wavelength of the coloured liquid and said light having a said wavelength shorter by a prescribed wavelength than the characteristic wavelength of the coloured liquid, a third comparator for obtaining the curvature of a transmittance curve from these differentials and a fourth comparator for comparing the curvature of said curve with a prescribed standard value for judgement.

6. A testing apparatus using a spectrophotometry of three wavelength values as claimed in claim 3, wherein said light receiving member comprises an aggregate of microlight receivers divided into a plural number of small sections corresponding to the detection limit of the foreign substance, one of said small sections of said aggregate being operatively associated with said three optical filter means for detection of said flaws in said vessel.

* * * * *